United States Patent
Sessions et al.

(10) Patent No.: US 6,794,554 B2
(45) Date of Patent: Sep. 21, 2004

(54) WOUND PACKING MATERIAL

(75) Inventors: Robert W. Sessions, Hinsdale, IL (US); Roy D. Carr, Burr Ridge, IL (US)

(73) Assignee: Ferris Pharmaceuticals, Inc., Burr Ridge, IL (US)

( * ) Notice: Subject to any disclaimer, the term of this patent is extended or adjusted under 35 U.S.C. 154(b) by 0 days.

(21) Appl. No.: 09/773,964

(22) Filed: Feb. 1, 2001

(65) Prior Publication Data

US 2001/0034499 A1 Oct. 25, 2001

Related U.S. Application Data

(60) Provisional application No. 60/179,565, filed on Feb. 1, 2000.

(51) Int. Cl.[7] ............................................... A61F 13/00
(52) U.S. Cl. .......................... 602/46; 602/43; 604/290
(58) Field of Search ..................... 602/41, 46; 420/136, 420/158; 604/1, 11–15

(56) References Cited

U.S. PATENT DOCUMENTS

| | | | | |
|---|---|---|---|---|
| 3,642,967 A | * | 2/1972 | Doll ............................. | 264/51 |
| 3,826,165 A | * | 7/1974 | Currie et al. .................. | 83/110 |
| 4,294,240 A | * | 10/1981 | Thill ............................ | 428/136 |
| 4,664,662 A | * | 5/1987 | Webster ....................... | 604/369 |
| 5,447,505 A | * | 9/1995 | Valentine et al. ............ | 604/304 |
| 5,606,760 A | * | 3/1997 | De Guzman .................. | 15/119 |
| 5,863,471 A | * | 1/1999 | Stanck ......................... | 261/107 |
| 5,868,724 A | * | 2/1999 | Dierckes et al. ............. | 604/368 |
| 5,899,871 A | * | 5/1999 | Cartmell et al. .............. | 602/43 |
| 6,284,346 B1 | * | 9/2001 | Sheridan ...................... | 428/156 |

* cited by examiner

Primary Examiner—Kim M. Lewis
(74) Attorney, Agent, or Firm—Leydig, Voit & Mayer, Ltd.

(57) ABSTRACT

Wound packing material comprising a resilient polymer-based foam sheet of a predetermined thickness. The foam sheet includes at least one slit of a predetermined length that extends from the foam surface into the foam to a predetermined depth. This slit, or slits, permits the foam, when folded upon itself, to occupy a smaller volume than the foam would occupy when folded over upon itself in the same manner, but in the absence of the slit.

12 Claims, 1 Drawing Sheet

FIGURE
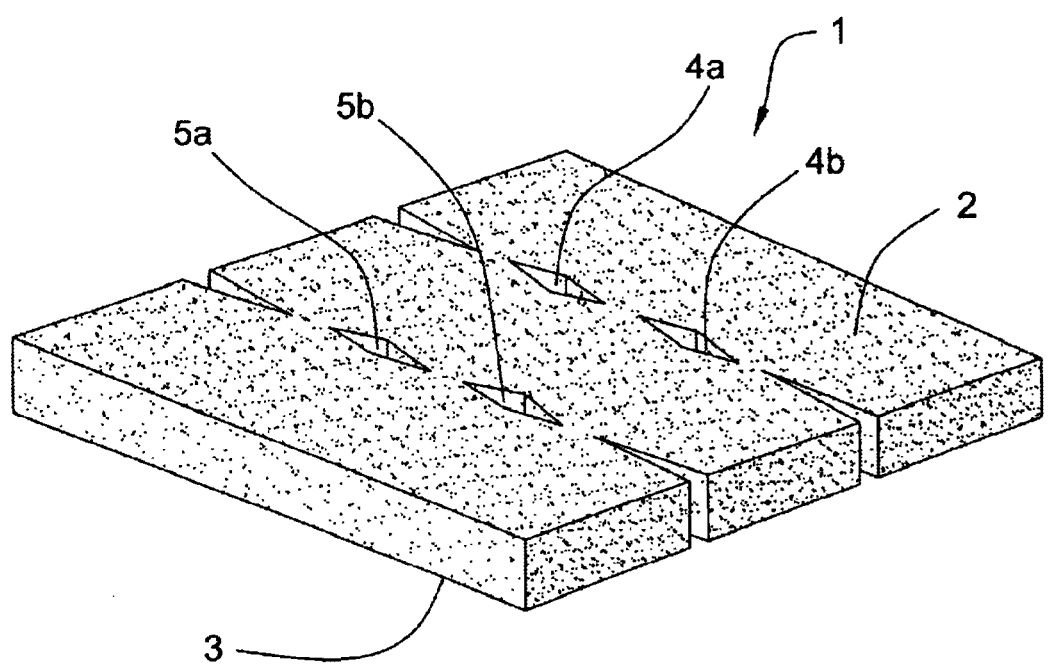

WOUND PACKING MATERIAL

CROSS-REFERENCE TO RELATED APPLICATIONS

This application claims the benefit of U.S. Provisional Patent Application No. 60/179,565, filed Feb. 1, 2000, and which is incorporated herein by reference.

FIELD OF THE INVENTION

The present invention relates generally to the field of wound dressings. More specifically, the invention pertains to wound packing materials.

BACKGROUND OF THE INVENTION

Over the years, the wound care industry has developed a wide variety of products designed to promote wound healing. Relatively recent developments include the introduction of polymer-based foams as absorbent material for wound dressings.

Polymer-based foams, such as urethane foams, are porous, permitting the absorption of fluids such as wound exudate, and flexible, permitting the dressings to adapt to contours of the wound and adjacent skin. Unlike conventional cloth-based absorbents, the foams are also resilient, i.e., when the foam is folded over upon itself, a permanent crease cannot be formed by hand pressure; the foam springs back into its original shape. This resiliency, however, is a hindrance to the use of such foams as wound packing materials. A sheet of resilient foam, when folded upon itself to create wound packing of a size appropriate for a particular wound, is difficult to retain in this configuration during insertion. One solution to this problem is provided in U.S. Pat. No. 4,664,662, wherein small pieces of foam are provided within a flexible, porous outer sack to form a wound packing product. This product can then be used to pack a wound by direct insertion. This product, however, cannot be readily resized or reshaped to provide an optimal fit to a particular wound.

Further problems in wound care have arisen due to the proliferation of wound dressings. For example, several dressing products stocked in medical facilities, upon visual inspection, may appear to be suitable for a particular use, but in fact may not be suitable, potentially leading to subsequent problems arising from improper treatment.

Thus, there exists a need for wound dressings that provide the advantages inherent in polymer-based foam dressings, but that also address the foregoing and other problems associated therewith.

SUMMARY OF THE INVENTION

The present invention meets the foregoing and other needs by providing, in one aspect, a wound packing material comprising a resilient polymer-based foam sheet of a predetermined thickness. The foam sheet includes at least one slit of a predetermined length extending into the foam to a predetermined depth. This slit, or slits, permits the foam, when folded upon itself, to occupy a smaller volume than the foam would occupy when folded over upon itself in the same manner in the absence of the slit. This is thought to be the result of the slit's effect of reducing the amount of material that binds the foam together, providing for a corresponding lessening in the foam's resistance to folding.

One benefit of the present invention is that it minimizes the amount of open space between folds, permitting a greater quantity of foam to be provided within a given volume. When inserted into a wound as a packing material, this relative increase in the quantity of foam within the wound provides for increased liquid absorption capacity over a given period of time, lengthening the time between dressing changes and enhancing wound healing. The present invention further requires less compressive force to maintain the foam sheet in a folded-over configuration, as compared to a foam sheet having the same formulation and dimensions without one or more slits. This permits a health care provider to more easily configure the foam sheet to match the dimensions of a given wound, and subsequently handle the folded packing material just prior to and during insertion into a wound. This advantage is particularly pronounced in a preferred configuration of the invention, wherein a plurality of substantially linear slits that extend through the entire thickness of the foam are provided, permitting a caregiver to readily customize the foam sheet to fit a variety of wounds.

The present invention further permits easy differentiation between dressings. For example, one viewing the slits in the packing material sheet, particularly those in the preferred embodiment that extend through the dressing, would likely not readily confuse such a packing material with a continuous foam sheet useful as a secondary wound covering, the latter being used to insure sterility of the wound.

These and other features and advantages of the various aspects of the present invention will be more readily apparent upon reading the following description of a preferred exemplified embodiment of the invention and upon reference to the accompanying drawings.

BRIEF DESCRIPTION OF THE DRAWING

The FIGURE is a perspective view of a preferred embodiment of the inventive wound packing material, wherein a plurality of slits are oriented along at least two substantially parallel lines, the slits extending entirely through the material.

DETAILED DESCRIPTION OF THE PREFERRED EMBODIMENTS

While the invention will be described and disclosed in connection with certain preferred embodiments and procedures, it is not intended to limit the invention to those specific embodiments. Rather it is intended to cover all such alternative embodiments and modifications as fall within the spirit and scope of the invention.

Turning initially to the FIGURE, there is depicted a preferred embodiment of the wound dressing of the present invention. The principal component of the wound dressing is a porous foam 1. For purposes of the present invention, the precise composition of the porous foam is not critical, although the composition should be selected that provides a porous foam that absorbs liquid, such as wound exudate. The porous foam should also be resilient. In particular, the foam, when folded upon itself, a permanent crease cannot be formed in the foam by hand force; the foam springs back into its original shape. Preferably, the foam is open-celled, with both upper 2 and lower 3 surfaces of the foam being free of any substrate used in the foam manufacturing process, permitting maximum liquid absorption by the open-celled foam.

Foams suitable for use in the present invention include those formed by the reaction of one or more monomers, oligomers or other polymers with one another, or with other reactive components. Illustrative of suitable foams include hydrophilic urethane foams, such as those described in U.S. Pat. Nos. 4,884,563, 5,064,653, 5,065,752 and 5,254,301.

The foams may include additional optional components, such as absorbent powders and adjuvants.

The foam, after it is prepared, is provided in the form of a sheet having a certain thickness. While the thickness of the foam is not critical, a thickness ranging from about 1/16 to about 1/2 inch is preferred to provide sufficient bulk when the dressing is used as a packing material. A sheet of about 1/8 to about 1/4 inch in thickness is most preferred.

As shown in the FIGURE, the packing material is a sheet containing at least one slit 4a, 4b, 5a, 5b which extends from a surface of the foam sheet at least partially into the foam. Preferably, a plurality of slits 4a, 4b, 5a, 5b are provided. Compared to a continuous foam sheet dressing, the slits permit the dressing to be folded into a relatively compact configuration, provide further enhancements in handling the folded dressing and other advantages, as previously discussed.

When the slits extend partially through the foam, the foam should be folded so that the slit is oriented on the outward face of the foam sheet for maximum benefit. The depth of the slit should advantageously be about equal to or greater than 1/2 of the foam thickness. Preferably, however, the slits extend through the entire thickness of the foam. Combinations of slits extending partially through the foam, and slits extending entirely through the foam, are contemplated by the present invention.

Advantageously, and as shown in the FIGURE, the plurality of slits 4a, 4b are oriented substantially along at least one line. Preferably, and as illustrated in a preferred embodiment shown in the FIGURE, the plurality of slices are oriented into at least two substantially parallel lines, 4a, 4b and 5a, 5b, permitting a caregiver additional means of configuring the dressing to meet the dimensions of the wound cavity. Alternatively, the plurality of lines formed by the slits may be oriented with respect to one another in any desirable manner, e.g., crossing one another at right angles, at 45 degree angles, or combinations of the foregoing.

Preferably, and to maximize ease in folding and retention of this configuration, the ratio of slit length to foam thickness may be at least about 1:1, and preferably at least about 2:1. The length of each slit, in absolute terms, may range from about 1/8 inch to a length just short of the width of the packing material, but will preferably range from about 1/4 inch to about 1 inch.

In a packing material having more than one slit, the spacing between each slit may range from about 1/2 inch to about 3 times the thickness of the foam sheet, with a spacing of from about 1/2 to about 2 times the sheet thickness being preferred. In absolute terms, the spacing may range from about 1/16 to about 1 inch, with spacing of about 1/8 to about 1/2 inch being preferred.

Any patents and articles referenced herein are incorporated by reference. Further, any reference herein to a component in the singular is intended to indicate and include at least one of that particular component, i.e., one or more.

Novel and improved polymer-based foam wound packing materials have been provided by the present invention which exhibit enhanced properties as compared to existing wound packing materials. Various additional modifications of the embodiments specifically illustrated and described herein will be apparent to those skilled in the art, particularly in light of the teachings of this invention. The invention should not be construed as limited to the specific form as shown and described, but instead is set forth in the following claims.

What is claimed is:

1. A method of treating a wound requiring insertion of a packaging material therein comprising
   a) providing a resilient, liquid absorbent, porous, polymer-based foam sheet of a predetermined thickness having at least one slit of a predetermined length extending into the foam to a predetermined depth,
   b) folding the foam over upon itself about the at least one slit such that the foam occupies a smaller volume then the foam would occupy when folded over upon itself in the same manner but in the absence of the at least one slit, and
   c) inserting the folded foam into the wound.

2. The method of treating a wound of claim 1 wherein the at least one slit extends through the predetermined thickness of the foam.

3. The method of treating a wound of claim 1 wherein the foam comprises a plurality of slits extending into the foam.

4. The method of treating a wound of claim 3 wherein the plurality of slits are oriented along at least one line.

5. The method of claim 3, the length of each slit ranges from about 1/8 inch to about 1 inch.

6. The method of claim 5, wherein a plurality of slits is along at least one line.

7. The method of claim 6, wherein a plurality of slits extends through the predetermined thickness of the foam.

8. The method of claim 6, wherein the length of each slit ranges from about 1/8 inch to about 1 inch.

9. The method of claim 8, wherein a plurality of slits is oriented along at least one line.

10. The method of claim 8, wherein a plurality of slits extends through the predetermined thickness of the foam.

11. The method of treating a wound of claim 1 wherein the resilient polymer-based foam is a urethane foam.

12. The method of claim 1, wherein the length of each slit ranges from about 1/8 inch to about 1 inch.

* * * * *